United States Patent [19]
Ho et al.

[11] Patent Number: 5,521,200
[45] Date of Patent: May 28, 1996

[54] 2-OXO-PYRROLO[1,2-A]BENZIMIDAZOLE-3-CARBOXYL DERIVATIVES USEFUL IN TREATING CENTRAL NERVOUS SYSTEM DISORDERS

[76] Inventors: Winston Ho, 105 Magella Ct., North Wales, Pa. 19454; Bruce E. Maryanoff, 3204 Aquetong Rd., New Hope, Pa. 18938; David F. McComsey, 1125 Victoria Rd., Warminster, Pa. 18974; Samuel O. Nortey, 7423 Euston Rd., LaMott, Pa. 19126

[21] Appl. No.: 332,687

[22] Filed: Nov. 1, 1994

Related U.S. Application Data

[63] Continuation of Ser. No. 175,705, Dec. 30, 1993, abandoned.

[51] Int. Cl.$^6$ .................................................. A61K 31/415
[52] U.S. Cl. ...................... 514/338; 514/394; 514/231.5; 514/245; 514/256; 514/310; 514/313; 514/314; 514/322; 544/139; 546/143; 546/159; 546/199; 546/273.1; 548/181; 548/214; 548/302.4
[58] Field of Search ...................... 514/394, 338; 546/271, 143, 159, 199; 548/302.4, 181, 214; 544/139

[56] References Cited

U.S. PATENT DOCUMENTS 5,246,955 9/1993 Skibo et al. ............................. 514/394

OTHER PUBLICATIONS

Ohta, S. et al., Chem. Pharm. Bull., 39(11), pp. 2787–2792, 1991.

Chemical Abstracts, vol. 99, No. 25, abstract 212531t. 1983.

Ohta, S. et al., Heterocycles, vol. 32, No. 10, pp. 1923–1931, 1991.

El–Ghazzawi, E. et al., J. Heterocyclic Chemistry, vol. 25, No. 4, pp. 1087–1093, 1988.

*Primary Examiner*—Jacqueline Haley

[57] ABSTRACT

A compound of the general formula I;

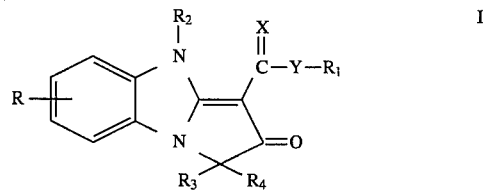

is disclosed as useful in treating disorders of the central nervous system. Pharmaceutical compositions and methods of treatment are also disclosed.

17 Claims, No Drawings

2-OXO-PYRROLO[1,2-A]BENZIMIDAZOLE-3-CARBOXYL DERIVATIVES USEFUL IN TREATING CENTRAL NERVOUS SYSTEM DISORDERS

This application is a continuation of U.S. Ser. No. 08/175,705, filed Dec. 30, 1993, now abandoned.

BACKGROUND OF THE INVENTION

The gamma-aminobutyric acid-A receptor (GABA-A receptor) is the most abundant inhibitory receptor in mammalian brain. It is comprised of a heteropolymeric structure that forms a chloride ion channel, and bears multiple recognition sites for the binding of modulatory molecules. The binding of GABA to its specific recognition site on the GABA-A receptor opens the ion channel and allows chloride ions to flow into the nerve cell. This action hyperpolarizes the cell membrane of that neuron and thereby makes the cell less reactive to excitatory stimuli. The chloride ion current may also be regulated by various drugs that serve as positive or negative modulators of the GABA-A receptor (Puia, G. et al. *Molecular Pharm.* 1991, 39, 691). The so-called benzodiazepine (BZD) receptor is a site for such allosteric modulators on the GABA-A receptor. This site mediates two opposing effects, one that amplifies the action of GABA ("positive" efficacy) and the other that reduces the action of GABA ("negative" efficacy). Agents facilitating GABA-receptor/chloride ion-channel functions via the BZD site are referred to as agonists, while agents reducing such function are referred to as inverse agonists. Antagonists at this site block the effects of agonists or inverse agonists by competitively inhibiting their binding. It is thus possible to have a series of compounds in which members equally bind to the BZD site but have equal and opposite regulatory effects on the GABA-A receptor/chloride ion channel. Also, within the series a continuum of activity is possible (Takada, S. et al. *J. Med. Chem.* 1988, 31, 1738). Thus, BZD receptor ligands can induce a wide spectrum of pharmacological effects ranging from muscle relaxant, hypnotic, sedative, anxiolytic, and anticonvulsant activities, produced by full or partial agonists ("positive"), to the proconvulsant, anti-inebriant, and anxiogenic activities, produced by inverse agonists ("negative"). (A further understanding of this area can be gleaned from: Mohler, H. *Arzneim.Forsch./Drug Res.* 1992, 42 (2a), 211; Haefely, W. et al., *Advances in Drug Research*, Academic Press, vol. 14, 1985, pp. 165–322; Skolnick, P. et al., *GABA and Benzodiazepine Receptors*, Squires, R., Ed., 1987, pp. 99–102 and references cited therein.)

The benzodiazepines are a class of compounds which bind to the BZD receptor with high affinity. Most of the drugs in use are agonist-type ligands for the receptor. Such compounds are generally useful for their anticonvulsant, anxiolytic, sedative, and muscle relaxant effects. Antagonists of the BZD binding site are useful for the treatment of benzodiazepine drug overdose and inverse agonists are useful in managing alcoholism.

The present invention is concerned with novel compositions of matter based on 2-oxo-pyrrolo[1,2-a]benzimidazole-3-carboxyl and derivatives. Compounds having some structural similarity to those of the present invention are described in Rida, S. M. et al. *J. Het. Chem.* 1988, 25, 1087; Soliman, F. S. G. et al. *Arch. Pharm.* 1984, 317, 951; Volovenko, Y. M. et al. U.S.S.R. Patent SU 1027166 (*Chem Abs.* 99(25) 212524t); Ohta, S. et al. *Heterocycles* 1991, 32, 1923; Ohta, S. et al. *Chem. Pharm. Bull* 1991, 39, 2787.

SUMMARY OF THE INVENTION

The present invention is directed to compounds of the following formula I:

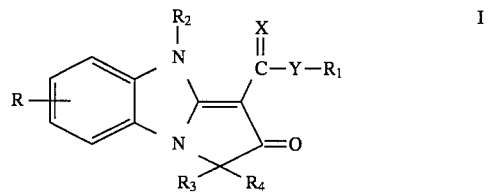

wherein R, $R_1$, $R_2$, $R_3$, $R_4$, X, and Y are as defined hereinafter. The compounds of formula I are useful in treating central nervous system disorders. The compounds are ligands for the BZD binding site on GABA-A receptors, and are thus useful as muscle relaxants, hypnotics/sedatives including sleep-aids, anxiolytics, anticonvulsants/antiepileptics, anti-inebriants, and antidotes for drug overdose (particularly benzodiazepine overdose).

The present invention also comprises pharmaceutical compositions containing one or more of the compounds of formula I and methods for the treatment of disorders to the central nervous system including convulsions such as epileptic seizures, anxiety, muscular spasms, sleep disorders, and benzodiazepine overdoses employing a compound of formula I.

DETAILED DESCRIPTION OF THE INVENTION

More specifically, the invention is directed to compounds of the following formula I:

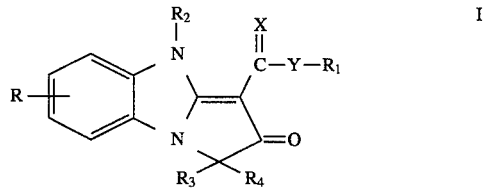

wherein
$R_1$ is selected from any of alkyl ($C_1$-$C_{12}$), cycloalkyl ($C_3$-$C_{10}$), phenyl; substituted phenyl where there are one or more substituents which are independently selected from any of halogen, alkyl ($C_1$-$C_5$), perfluoro(lower)alkyl, nitro, lower alkoxy, hydroxy, amino, lower alkylamino, di(lower alkyl)amino, carboxy, lower alkoxycarbonyl, aminocarbonyl, lower alkylthio, cyano, and aminosulfonyl; aralkyl and substituted aralkyl where the aryl substituents are as described above with respect to substituted phenyl; a heterocycle where the heterocycle is selected from any of pyridine, thiazole, thiophene, furan, indole, benzothiophene, pyridazine, pyrimidine, indole, indoline, quinoline, indazole, imidazole, benzofuran, triazine, pyrazine, isoquinoline, isoxazole, thiadiazole, benzothiazole, triazole or benzotriazole; a substituted heterocycle where there are one or more substituents which are independently selected from any of halogen, perfluoro(lower)alkyl, nitro, lower alkylthio, lower alkoxy, lower alkyl, di(lower alkyl)amino, carboxy, lower alkoxycarbonyl, piperidin-3-yl, piperidin-4-yl, morpholin-4-yl, heterocyclic—$CH_2$—, heterocyclic—$CH_2CH_2$—, or substituted heterocyclic—$CH_2$— and heterocyclic—$CH_2CH_2$— (where the heterocycle is as previously defined and where the substituent groups are as previously defined for the heterocycle group). More preferably, $R_1$ is selected from any of alkyl ($C_1$-$C_{12}$), cycloalkyl ($C_3$-$C_{10}$), phenyl, substituted phenyl (where the substituents are independently selected from the group consisting of halogen, perfluoro(lower) alkyl, nitro, lower alkoxy, lower alkyl, hydroxy, amino, di(lower alkyl) amino, lower alkoxycarbonyl, lower alkylthio, cyano and aminosulfonyl), aralkyl, a heterocycle selected from any of pyridine, pyridinylmethyl, thiazole, pyrimidine, indoline, quinoline, indazole, benzofuran, triazine, pyrazine, isoquinoline, isoxazole, thiazole, thiadiazole, benzothiazole, triazole, or benzotriazole, or a substituted heterocycle from the preferred group of heterocycles which are pyridine, isoxazole, thiadiazole, and quinoline (where there is one or more substituents which are independently selected from any of halogen, perfluoro(lower) alkyl, nitro, lower alkylthio, lower alkoxy, lower alkyl, di(lower alkyl)amino, carboxy or lower alkoxycarbonyl).

$R_2$ is selected from any of hydrogen, alkyl ($C_1$–$C_{12}$), cycloalkyl ($C_3$–$C_{10}$), aralkyl and substituted aralkyl, where the aryl substituents are as previously defined in connection with the definition of $R_1$. $R_2$ is more preferably any of H, lower alkyl or aralkyl.

R is selected from one or more of hydrogen, alkyl ($C_1$–$C_8$), branched alkyl ($C_3$–$C_8$), halogens, perfluoro(lower alkyl), lower alkoxy, hydroxy, di(lower alkyl) amino, lower alkoxycarbonyl or lower alkylthio. There may be up to 4 independent R substituents on the phenyl. More preferably, R is selected from any of lower alkoxy, H, halogen or alkyl ($C_1$–$C_8$). Preferably, there is only one R substituent other than H.

$R_3$ and $R_4$ are independently selected from any of hydrogen, alkyl ($C_1$–$C_3$), or aralkyl ($C_7$–$C_9$).

X is selected from oxygen or sulfur.

Y is selected from NH, oxygen or sulfur.

Y and $R_1$ may also be taken together to form $NH_2$.

As used herein unless otherwise noted alkyl and alkoxy whether used alone or as part of a substituent group, include straight and branched chains. For example, alkyl radicals include methyl, ethyl, propyl, isopropyl, butyl, isobutyl, sec-butyl, t-butyl, pentyl, 2-methyl-3-butyl, 1-methylbutyl, 2-methylbutyl, neopentyl, hexyl, 1-methylpentyl, 3-methylpentyl. Alkoxy radicals are oxygen ethers formed from the previously described straight or branched chain alkyl groups. Unless otherwise noted, "lower" when used with alkyl and alkoxy means a carbon chain composition of 1–5 carbon atoms. Of course, if the alkyl or alkoxy substituent is branched there must be at least 3 carbons.

The term "aryl" as used herein alone or in combination with other terms indicates aromatic hydrocarbon groups such as phenyl or naphthyl. The term "aralkyl" means a radical containing a lower alkyl group substituted with an aryl radical. With reference to substituents, the term independently means that when more than one of such substituent is possible, such substituents may be the same or different from each other.

The definition of formula I as shown in the specification and as used in the claims includes possible isomers, such as tautomers and rotamers. The formulas Ia and Ib illustrate this point, for the case when $R_2$ is H.

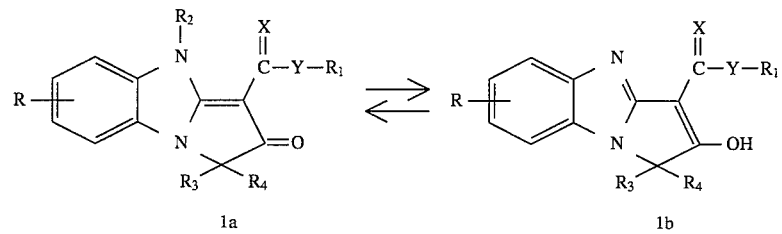

Examples of particularly preferred compounds of formula I include:

N-(4-Pyridyl)-1,2-dihydro-2-oxo-4H-pyrrolo [1,2-a]benzimidazole-3-carboxamide, i.e., where R, $R_2$, $R_3$ and $R_4$ are hydrogen, $R_1$ is 4-pyridyl, Y is NH, and X is oxygen in formula I.

N-(4-Dimethylaminophenyl)-1,2-dihydro-2-oxo-4H-pyrrolo[1,2-a]benzimidazole- 3-carboxamide, i.e., where R, $R_2$, $R_3$ and $R_4$, are hydrogen, $R_1$ is 4-dimethylaminophenyl, Y is NH, and X is oxygen in formula I.

N-(2,5-Difluorophenyl)-1,2-dihydro-2-oxo-4H-pyrrolo [1,2-a]benzimidazole-3-carboxamide, i.e., where R, $R_2$, $R_3$ and $R_4$ are hydrogen, is 2,5-difluorophenyl, Y is NH, and X is oxygen in formula I.

N-(2,4,6-Trifluorophenyl)-1,2-dihydro-2-oxo-4 H-pyrrolo[1,2-a]benzimidazole-3-carboxamide, i.e., where R, $R_2$, $R_3$ and $R_4$ are hydrogen, $R_1$ is 2,4,6-trifluorophenyl, Y is NH, and X is oxygen in formula I.

N-(2,6-Difluorophenyl)-1,2-dihydro-2-oxo-4H-pyrrolo [1,2-a]benzimidazole-3-carboxamide, i.e., where R, $R_2$, $R_3$ and $R_4$ are hydrogen, $R_1$ is 2,6-difluorophenyl, Y is NH, and X is oxygen in formula I.

N-(2,6-Difluorophenyl)-1,2-dihydro-2-oxo-1,1,4-trimethylpyrrolo[1,2-a]benz-imidazole-]3-carboxamide, ie, where R, is hydrogen, $R_2$, $R_3$ and $R_4$ are methyl, $R_1$ is 2,6-difluorophenyl, Y is NH, and X is oxygen in formula I.

N-(2,6-Difluorophenyl)-1,2-dihydro-2-oxo-4-ethylpyrrolo[1,2-a]benzimidazole-3-carboxamide, ie, where R, $R_3$ and $R_4$ are hydrogen, $R_2$ is ethyl, $R_1$ is 2,6-difluorophenyl, Y is NH, and X is oxygen in formula I.

N-(2,4-Difluorophenyl)-1,2-dihydro-2-oxo-4H-pyrrolo [1,2-a]benzimidazole-3-carboxamide, ie, where R, $R_2$, $R_3$, $R_4$ are hydrogen, $R_1$ is 2,4-difluorophenyl, Y is NH, X is oxygen in formula I.

When compounds contain a basic moiety, acid addition salts may be prepared and may be chosen from hydrochloric, hydrobromic, hydroiodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, p-toluenesulfonic, cyclohexanesulfamic, salicylic, 2-phenoxybenzoic, 2-acetoxybenzoic, or saccharin, and the like. Such salts can are made by reacting the free base of compounds of formula I with the acid and isolating the salt.

Compounds of formula I can also be treated with a base to prepare the salt of the enolate formed. Such pharmaceutically acceptable salts may include but are not restricted to: alkali metal salts such as sodium or potassium; ammonium salts; monoalkylammonium salts; dialkylammonium salts; trialkylammonium salts; tetraalkylammonium salts; and tromethamine salts.

Hydrates and other solvates of the compound of formula I are also included within the scope of this invention and included within the definition of formula I.

The compounds of formula I are prepared as outlined in the following scheme.

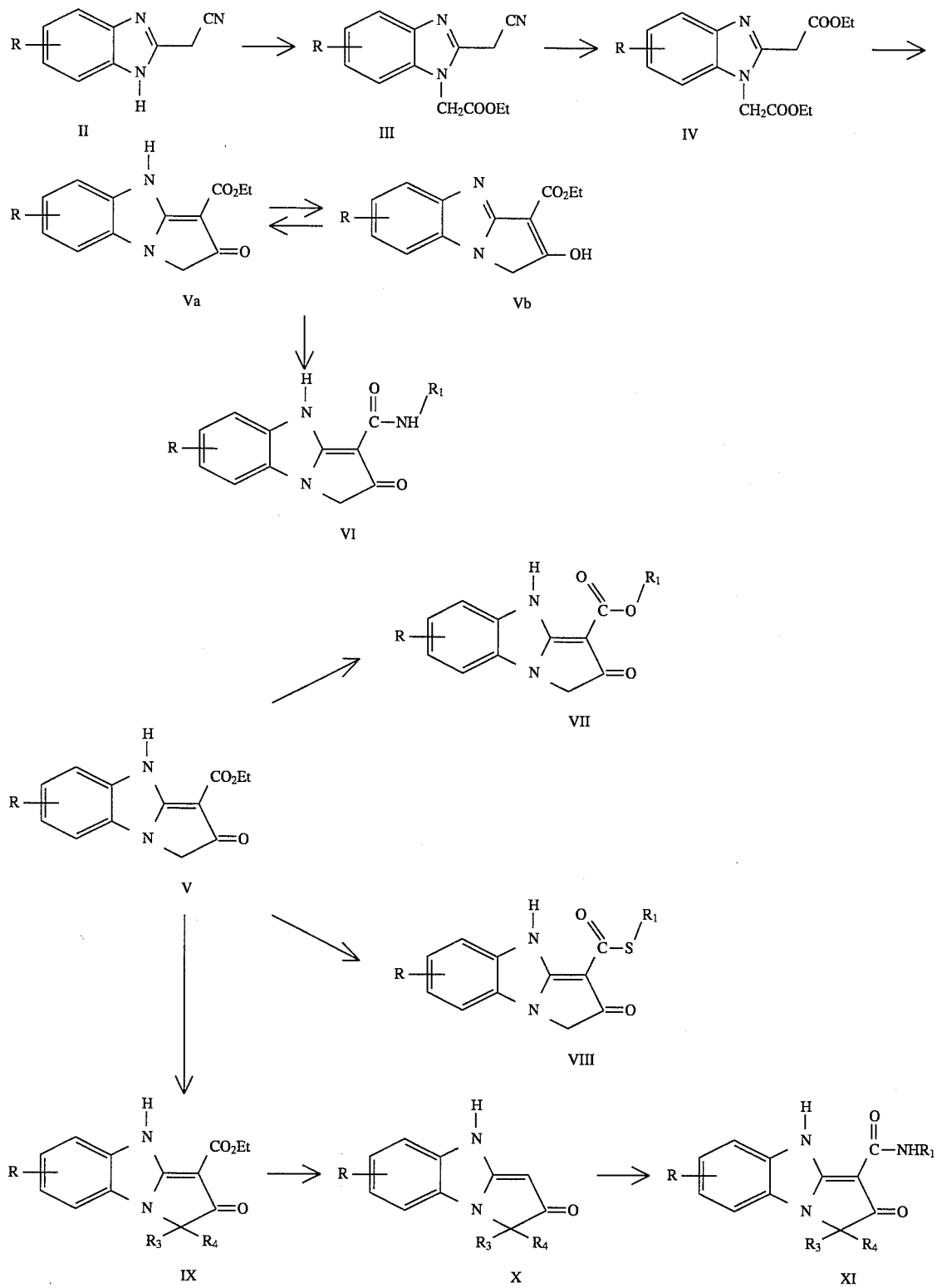

More specifically, the substituted 2-benzimidazolylacetonitrile derivative II, commercially available (e.g.; Aldrich Chemical Co.) or prepared by standard methods known in the art, is treated with a mixture of ethyl bromoacetate and a suitable base such as triethylamine in an appropriate solvent such as dimethylformamide at room temperature for 1–4 days to give the desired nitrile derivative III. The cyano group of the derivative III is hydrolysed to give the diester derivative IV by treatment of III with anhydrous acid such as HCl(g) in an appropriate solvent such as EtOH at reflux for about 4–24 h.

The diester is treated with a suitable base such as sodium ethoxide in an appropriate solvent such as EtOH for about 12–24 h at room temperature followed by treatment with ethanolic HCl to give pyrrolobenzimidazole V (shown as enol and keto tautomers Va and Vb).

The pyrrolobenzimidazole derivative V is heated to reflux with the appropriate substituted amine derivative (commercially available or prepared via methods known in the art; for example, see Turner, J. *Journal Of Organic Chemistry* 1983, 48, 3401–3408) in a suitable solvent such as xylene for about 1–24 h to give the desired pyrrolo[1,2-a]benzimidazole derivative VI (which also has keto amide and enol amide forms, only one of which is shown).

Alternatively the pyrrolobenzimidazole derivative V is heated to reflux with the appropriate substituted phenol or thiophenol for about 4–24 h to give the corresponding carboxylate and thiocarboxylate derivatives, VII and VIII.

The alkylated pyrrolobenzimidazole derivative IX is prepared by treating the pyrrolobenzimidazole derivative V with an appropriate alkylating agent such as ethyl iodide and a suitable base such as sodium hydride in an appropriate solvent such as DMF at about 0° C. to room temperature for about 1–24 h. Base catalyzed hydrolysis and decarboxylation (in refluxing ethanol) of the alkylated derivative IX gives the keto derivative X. Treatment of such keto derivative with a suitable electrophile such as 2-fluorophenyl isocyanate at room temperature for 2–24 h gives the corresponding keto amido derivative XI.

The compounds of this invention were tested for affinity for the benzodiazepine sites of the GABA-A receptor. Since compounds which bind to this receptor can be useful in treating central nervous system disorders, the compounds were also tested in appropriate screens to evaluate specific activities. The results of the various screens are shown in Table 1. Not all compounds were tested in each of the screens. A blank next to a particular compound indicates that the compound was not tested in that screen.

Benzodiazepine Receptor Binding Assay

Selected compounds, which were prepared according to the experimental details given in the following examples, were tested for binding to the benzodiazepine site of the GABA-A receptor (Williams, M. et al., *J. Pharm. Exper. Therap.* 1988, 248, 89). The ability of the compounds of the invention to inhibit the binding of flunitrazepam to prepared receptors was assessed. For each sample, membranes from ca. 10 mg of tissue were incubated in a $K_2HPO_4$-buffered incubation medium (final concentration=2.0 mL). The concentration of ligand ($^3$H-flunitrazepam) was ca. 3 nM. Samples were incubated 10–20 min at 25° C., after which the membrane material and bound ligand was collected on glass fiber filter sheets using vacuum filtration. The collected material was washed with 10 mM HEPES buffered solution, and the radioactivity associated with each sample was measured by liquid scintillation spectrometry. The binding of the test drug to the receptor was determined by comparing the amount of radiolabeled ligand bound in control samples to the amount of ligand bound in the presence of the drug. Concentration-response data were analyzed in a variety of ways. The $IC_{50}$ was usually calculated by transforming the data to a log-logit format, then performing a linear regression analysis. This procedure provides a Hill coefficient as well as the $IC_{50}$ value. The $IC_{50}$ value, for all tested compounds is listed in Tables 1. An $IC_{50}$ value of over 10,000 for a particular compound indicates that the compound was not active in this screen. This screen is a general screen and compounds active in this screen are considered active in treating one or more disorders of the central nervous system.

Assay to Measure the Suppression of Anxiety in the Adult Male Rat

The anxiolytic activity of selected compounds of the invention was assessed by determining their ability to release (disinhibit) behavior that had been suppressed by punishment (Vogel, J. R. et al. *Psychopharmacology* 1971, 21, 1). Male rats were deprived of water for 48 hours and were deprived of food for 24 hours prior to testing. After the first 24 hours of water deprivation, they were placed in the conflict chamber for a training period; wherein, they were allowed 200 unpunished licks from a bottle containing tap water. The experiment was run the next day. At the expected time of peak activity, the animals were placed in the chamber and allowed access to tap water. If they failed to drink, the experiment was terminated in 5 min, and animals were evaluated for signs of CNS depression. Their first lick initiates a 3-min test session. Subsequently, every 20th lick was punished by a 0.2-s shock delivered via the stainless-steel drinking-tube. Vehicle-treated control animals generally were willing to accept a median number of 3 to 8 shocks per test session. Animals treated with an active anxiolytic drug tolerated significantly more shocks than control animals. The Wilcoxon rank-sum test (Mann-Whitney U-test) was used to test for an increase ($p<0.05$, 1-tailed) in the median number of shocks in drug-treated groups, compared to a concurrently run vehicle-treated group. The biological assay is considered to be valid if the effects of a known anxiolytic (positive control) are detected, within the same experiment. A compound was considered active if there is a significant difference in the median number of shocks tolerated between the drug-treated group and the control group. The minimum effective doses (MED) for the active compounds of the invention are listed in Tables 1. The MED was defined as the minimum dose of the drug-treatment as analyzed using the Wilcoxon rank-sum test (SAS; Statistical Analysis System, version 5.16). If the MED value is greater than 10, an active dose of the compound being tested had not been determined.

Assay to Determine the Suppression of Metrazol-Induced Convulsions in Adult Male Rats and Mice Selected compounds of the invention were tested for their ability to reduce metrazol-induced convulsions in mice (Swinyard, E. A. *J. Am. Pharm Assoc.* 1949, 38, 201). Male $CD_1$ mice, were fasted at least 16 hours, were divided into equal groups and test compounds or vehicle were administered parenterally. Water was not withheld except during the period of observations. At the time of suspected peak activity, anti-pentylenetetrazol (anti-metrazol) activity was evaluated by the subcutaneous administration of the $CD_{90}$ dose of metrazol (the dose of metrazol was determined from the dose-response curve producing clonic convulsions in 90% of animals that received the corresponding vehicle for this experiment). Metrazol was dissolved in 0.9% sodium chloride solution, and its dose volume was 10 ml/kg. Animals were housed individually for observation of clonic convulsions, tonic convulsions and death for a period of 30 min. Test compounds that blocked the clonic seizure component of the convulsion in at least 50% of the animals were considered active. The biological assay was considered to be valid if the effects of a known anticonvulsant (positive control) were detected, within the same experiment. Activity was reported as percent reduction of clonic convulsions from the vehicle group. The $ED_{50}$ values of active compounds were calculated by the method of probits (Finney, D. J. 1971. Probit Analysis. London: Cambridge University Press) and are listed in Tables 1. An $ED_{50}$ value of greater than 30 indicates that an active dose for the compound being tested had not been determined. Compounds active in this screen are considered active anticonvulsion/antiepileptic agents. To date, compound numbers 3, 7 and 8 have not been found to be active in the screens in which they have been tested.

tion may be administered in an amount of from about 0.2 to 25 mg/kg per day. In therapeutic use as an anxiolytic, the compounds of the invention may be administered in an amount from about 0.2 to 25 mg/kg per day. In therapeutic use as an anticonvulsant/antiepileptic, the compounds of the invention may be administered in an amount from about 0.2 to 25 mg/kg per day. In therapeutic use as an agent for treating benzodiazepine overdoses, the compounds of the invention may be administered in an amount from about 0.2 to 25 mg/kg per day. In therapeutic use as a sedative/hypnotic, a therapeutically effective amount is from about 0.2 to 25 mg/kg per day. As a muscle relaxant about 0.2 to 25 mg/kg per day of the compounds of this invention may

TABLE 1

| CP # | $R_1$ | $R_2$ | $R_3$ | $R_4$ | R | $IC_{50}$ (nM) | Conflict (ip) MED (mg/kg) | Metrazol (ip) $ED_{50}$ (mg/kg) |
| --- | --- | --- | --- | --- | --- | --- | --- | --- |
| 1 | 4-pyridyl | H | H | H | H | 7220 | >10 | >10 |
| 2 | 4-Me$_2$NPh | H | H | H | H | 1741 | >10 | >30 |
| 3 | 2,5-F$_2$Ph | H | H | H | H | >10000 | >10 | >300 |
| 5 | 2,6-F$_2$Ph | H | H | H | H | 80.1 | <10 | 6.0 |
| 6 | 2,6-F$_2$Ph | Me | Me | Me | H | >10000 | >10 | 1–10 |
| 7 | 2,6-F$_2$Ph | Et | H | H | H | >10000 | >10 | >10 |
| 8 | 2,4-F$_2$Ph | H | H | H | H | >10000 | >10 | >300 |

To prepare the pharmaceutical compositions of this invention, one or more compounds or salts thereof, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet, capsule, powder, injection, teaspoonful and the like, from about 5 to about 500 mg of the active ingredient, although other unit dosages may be employed.

In therapeutic use in treating disorders of the central nervous system in mammals, the compounds of this invenbe used. Determination of optimum dosages for a particular situation is within the skill of the art.

EXAMPLES

The following examples describe the invention in greater detail and are intended to illustrate the invention, but not to limit it.

Melting point determinations were carried out on a Thomas Hoover or Mel-Temp melting point apparatus and are corrected unless otherwise specified. Each compound has at least two analytical results (elemental analysis, IR, $^1$H NMR, MS) that are consistent with its assigned structures. Nuclear magnetic resonance (NMR) spectra for hydrogen atoms were measured in the indicated solvent with tetramethylsilane (TMS) as the internal standard on a Bruker AM-360 (360 MHz), AM-400 (400 MHz), or AT-300 (300 MHz) spectrometer. The values are expressed in parts per million downfield from TMS. The elemental analyses are expressed in percentage by weight of each element per total molecular weight. The mass spectra (MS) were determined on a Finnigan 3300 spectrometer (methane), using desorption chemical ionization techniques. All preparative column chromatography was run using a Waters Prep 500A HPLC (silica gel) employing the appropiate commercially available solvent. Unless otherwise noted, the materials used in the examples were obtained from readily available commercial suppliers or synthesized by standard methods known to anyone skilled in the art of chemical synthesis. The substituents groups, which vary between examples are hydrogen unless otherwise noted.

EXAMPLE 1

N-(4-Pyridyl)-1,2-dihydro-4H-pyrrolo[1,2-a]benzimidazole-3-carboxamide-2(1H)-one (CP #1)

A solution of 2-benzimidazolylacetonitrile (10.0 g, 0.06 mol) in triethylamine (70 ml) was warmed to 30° C., and treated with ethyl bromoacetate (30 g, 0.18 mol). After stirring at 65° C. for 5 h, the reaction mixture was allowed to stir at room temperature for 24 h, treated with water and extracted into ethyl acetate. The organic extract was washed with brine, dried ($Na_2SO_4$), filtered and concentrated under reduced pressure to a thick syrup. The crude mixture was purified via preparative HPLC (ethyl acetate/hexane; 1:1), to give III (2.38 g, 16%) as a dark brown solid.

A solution of the nitrile derivative III (2.20 g, 0.009 mol) in 6N HCl/EtOH (65 ml) was stirred at room temperature for 24 h, and concentrated to a syrup which was dissolved in $H_2O$, treated with aqueous NaOH to pH=8, extracted into ethyl acetate, dried, ($Na_2SO_4$), and solvent removed under reduced pressure to give desired diester IV (2.15 g, 82%) as a dark brown solid. Sodium (0.16 g, 6.9 mmol) was added to a stirred solution of absolute EtOH (10.0 ml) under an argon atmosphere. An additional portion of EtOH (10.0 ml) was added to the reaction mixture followed by the dropwise addition of a solution of the diester derivative IV (1.85 g, 6.30 mmol) in EtOH (10 ml). The mixture was stirred overnight at room temperature and the resulting solid precipitate was filtered, washed with additional EtOH and air dried. This solid was suspended in water and the pH was adjusted to 7.9 by the addition of 1N HCl. This mixture was stirred for 1 h and the resulting solid was isolated (filtered) and air dried to give ethyl 1,2-dihydro-4H-pyrrolo[1,2-a]benzimidazole- 3-carboxylate V as a solid: mp 269°–271° C.

Anal. Calcd for $C_{13}H_{12}N_2O_2$C, 63.93; H, 4.92; N, 11.47 Found: C, 63.58; H, 4.93; N, 11.50

The pyrrolobenzimidazole derivative V (1.08 g, 4.4 mmol) and 4-aminopyridine (0.42 g, 4.5 mmol) were combined in xylenes (50 ml) and heated at reflux for 6 h in a flask fitted with a Dean Stark trap. The resulting solid was filtered from the cooled reaction mixture and recrystallized from a mixture of methylene chloride and MeOH to give the title compound 1 as a light brown hydrated crystalline solid: mp 317°–320° C.; Cl-ms: m/z 293 (M+1).

Anal. Calcd for $C_{16}H_{12}N_4O_2 \cdot 0.2 H_2O$: C, 64.95; H, 4.22; N, 18.93 Found: C, 64.64;H, 4.02; N, 18.81

The following general procedure was used in the synthesis of the compound Nos. 2–5, 8 listed in Table 2.

EXAMPLE 2

An appropriately substituted pyrrolobenzimidazole derivative V (1 molar equivalent) prepared as in Example 1 and a suitable amine (1.2–2.0 molar equivalents) were combined in xylenes (200 mL) and heated at reflux for 1–6 h in a flask fitted with a Dean Stark trap. The resulting solid was isolated from the reaction mixture and recrystallized from a suitable solvent to give the desired pyrrolobenzimidazole derivative VII as a solid.

TABLE 2

| CP # | $R_1$ | $R_2$ | $R_3$ | $R_4$ | R | mp, °C. | C | H | N | Empirical Formula |
|---|---|---|---|---|---|---|---|---|---|---|
| 1 | 4-pyridyl | H | H | H | H | 317–320 | 64.64 | 4.02 | 18.81 | $C_{16}H_{12}N_4O_2$[a] |
| 2 | 4-$Me_2$NPh | H | H | H | H | 288–289 | 67.97 | 5.49 | 16.59 | $C_{19}H_{18}N_4O_2$ |
| 3 | 2,5-$F_2$Ph | H | H | H | H | 340–341 | 62.33 | 3.29 | 12.77 | $C_{17}H_{11}F_2N_3O_2$ |
| 4 | 2,4,6-$F_3$Ph | H | H | H | H | 274–275 | 58.87 | 3.21 | 12.13 | $C_{17}H_{10}F_3N_3O_2$ |
| 5 | 2,6-$F_2$Ph | H | H | H | H | 279–280 | 61.65 | 3.31 | 12.66 | $C_{17}H_{11}F_2N_3O_2$[b] |
| 6 | 2,6-$F_2$Ph | Me | Me | Me | H | 228–229 | 65.37 | 4.85 | 11.06 | $C_{20}H_{17}F_2N_3O_2$ |
| 7 | 2,6-$F_2$Ph | Et | H | H | H | 283–284 | 64.53 | 4.01 | 11.71 | $C_{19}H_{15}F_2N_3O_2$ |
| 8 | 2,4-$F_2$Ph | H | H | H | H | 326–329 | 62.22 | 3.15 | 12.84 | $C_{17}H_{11}F_2N_3O_2$ |

Solvates present (moles): [a] 0.20 $H_2O$; [b] 0.1 $H_2O$.

EXAMPLE 3

N-(2,6-Difluorophenyl)-1,2-dihydro-1,1,4-trimethyl-4H-pyrrolo[1,2-a]benzimidazole-3-carbozamide-2(1H) one (CP #6)

A solution of benzimidazole-3-carboxylate V (3.0 g, 12.3 mmol) in DMF (150 mL) was treated with sodium hydride (60% in mineral oil, 0.68 g, 21.0 mmol), and the reaction mixture stirred for 20 min. Methyl iodide (3.98 g, 28 mmol) was cautiously added and the mixture allowed to stir for 18 h, after which the reaction mixture was concentrated to one half the volume, treated with chloroform, and filtered. The filtrate was washed with water, brine, dried ($Na_2SO_4$) and concentrated to give IX ($R_2/R_3/R_4$=Me; 1.08 g) as a pale brown solid. This solid (0.96 g, 3.4 mmol) was treated with 3N NaOH (12 mL) and EtOH (35 mL), and reaction mixture refluxed for 4 h, solvents evaporated off, treated with chloroform, washed with water, brine, dried ($Na_2SO_4$) and filtered. The filtrate was concentrated to give crude X ($R_2/R_3/R_4$=Me, 0.98 g) as a yellow semisolid. Cl-ms: m/z 215 (M+1). The trialkylated product (0.45 g, 2.0 mmol), was treated with 2,6-difluorophenyl isocyanate (0.36 g, 2.4 mmol) and $CH_2Cl_2$ (8.0 mL) and the mixture stirred for 24 h, concentrated to a solid which was recrystallized in $CH_2Cl_2$/MeOH twice to give pure title compound ($R_2/R_3/R_4$= Me, 0.30 g) as an orange solid: mp: 228°–229° C.; Cl-ms: m/z 370 (M+1).

Anal. Calcd for $C_{20}H_{17}F_2N_3O_2$ C, 65.03; H, 4.64; N, 11.38 Found: C, 65.37; H, 4.85; N, 11.06

EXAMPLE 4

N-(2,6-Difluorophenyl)-1,2-dihydro-4-ethyl-4H-pyrrolo[1,2-a]benzimidazole-3-carboxamide-2(1H)-one (CP #7)

A solution of benzimidazole-3-carboxylate V (3.0 g, 12.3 mmol) in DMF (150 mL) was treated with sodium hydride (60% in mineral oil, 0.82 g, 21.0 mmol), and the reaction mixture stirred for 30 min. Ethyl iodide was added dropwise, and the mixture allowed to stir for 18 h, after which the reaction mixture was concentrated down to one half the volume, treated with chloroform, and filtered. The filtrate was washed once with water, brine, dried ($Na_2SO_4$), and concentrated to a semisolid. It was subjected to preparative HPLC (ethyl acetate/hexane; 8:1) to give IX ($R_3/R_4$=H; 1.04 g) as a yellow solid. This solid (1.00 g, 3.6 mmol) was treated with 3N NaOH (12 mL) and EtOH (35 mL), and refluxed for 4 h, solvents evaporated off, treated with chloroform, and washed with water, brine, dried ($Na_2SO_4$), and filtered. The filtrate was concentrated to give X ($R_3/R_4$=H) as a light yellow solid (0.98 g), which was recrystallized in $CH_2Cl_2$/MeOH to give 0.76 g of pure sample. Cl-ms: m/z 201 (M+1). The N-alkylated product X (0.76 g, 3.8 mmol) was treated with 2,6-difluorophenyl isocyanate (0.612 g, 3.9 mmol) and $CH_2Cl_2$ (8.0 mL), and the mixture stirred for 3 h, concentrated to a solid which was subjected to preparative HPLC ($CH_2Cl_2$/MeOH; 10:1) to give the title compound (0.40 g) as a yellow solid: mp: 283°–284° C.; Cl-ms: 356 (M+1).

Anal. Calcd for $C_{19}H_{15}F_2N_3O_2$: C, 64.22; H, 4.25; N, 11.83 Found: C, 64.53; H, 4.01; N, 11.71

What is claimed is:

1. A compound of the following formula I:

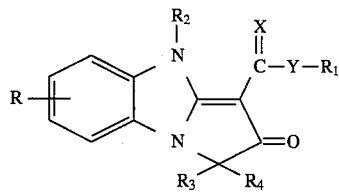

I wherein $R_1$ is selected from any of alkyl ($C_1$–$C_{12}$), cycloalkyl ($C_3$–$C_{10}$), phenyl, substituted phenyl, aralkyl, substituted aralkyl, a heterocycle wherein the heterocycle is selected from any of pyridine, thiazole, thiophene, furan, indole, benzothiophene, pyridazine, pyrimidine, indole, indoline, quinoline, indazole, imidazole, benzofuran, triazine, pyrazine, isoquinoline, isoxazole, thiadiazole, benzothiazole, triazole or benzotriazole, a substituted heterocycle, piperidin-3-yl, piperidin-2-yl, morpholin-4-yl, heterocyclic—$CH_2$— heterocyclic—$CH_2CH_2$—, or substituted heterocyclic—$CH_2$— and heterocyclic—$CH_2CH_2$—;

$R_2$ is selected from any of hydrogen, alkyl ($C_1$–$C_{12}$), cycloalkyl ($C_3$–$C_{10}$), aralkyl and substituted aralkyl;

R may be one or more substituents selected from the group consisting of any of hydrogen, alkyl ($C_1$–$C_8$), halogen, perfluoro(lower)alkyl, lower alkoxy, di(lower alkyl)amino, lower alkoxycarbonyl or (lower alkyl)thio;

$R_3$, $R_4$ are selected from hydrogen, alkyl ($C_1$–$C_3$), and aralkyl ($C_7$–$C_9$)

X is selected from oxygen or sulfur;

Y is selected from NH, oxygen or sulfur:

Y and $R_1$ may also be taken together to form an $NH_2$ group;

in the case of substituted phenyl and substituted aralkyl, there are one or more substituents which are independently selected from any of halogen, alkyl ($C_1$–$C_5$), perfluoro(lower)alkyl, nitro, lower alkoxy, hydroxy, amino, lower alkylamino, di(lower alkyl)amino, carboxy, lower alkoxycarbonyl, carboxamide, lower alkylthio, cyano, or aminosulfonyl;

in the case of substituted heterocycle and substituted heterocyclic—$CH_2$— and heterocyclic—$CH_2CH_2$—, there are one or more substituents, which are independently selected from any of halogen, perfluoro(lower)alkyl, nitro, lower alkylthio, lower alkoxy, lower alkyl, di(lower alkyl)amino, carboxy, or lower alkoxycarbonyl or a pharmaceutically acceptable salt, isomer or hydrate thereof.

2. The compound of claim 1, wherein $R_2$ is selected from any of H, lower alkyl or aralkyl.

3. The compound of claim 1, wherein there is one R substitutent.

4. The compound of claim 3, wherein R is selected from any of lower alkoxy, H, halogen, perfluorolower alkyl, or alkyl ($C_1$–$C_{12}$).

5. The compound of claim 1, wherein X is oxygen and Y is NH.

6. The compound of claim 1, wherein X is S and Y is NH.

7. The compound of claim 1, wherein X is oxygen and Y is S or O.

8. The compound of claim 1, selected from any of 1,2-dihydro-N-(4-dimethylaminophenyl)-2-oxo-pyrrolo[1,2-a]benzimidazole-3-carboxamide, 1,2-dihydro-N-(2-fluorophenyl)-2-oxo-pyrrolo[1,2-a]benzimidazole-3-carboxamide, 1,2-dihydro-2-oxo-N-(2,4,6-trifluorophenyl)pyrrolo[1,2-a]benzimidazole-3-carboxamide, 1,2-dihydro-N-(2,6-difluorophenyl)-2-oxo-pyrrolo[1,2-a]benzimidazole-3-carboxamide, 1,2-dihydro-2-oxo-1,1,4-trimethyl-N-(2,6-diflourophenyl)pyrrolo[1,2a]benzimidazole-3-carboxamide, 1,2-dihydro-2-oxo-4-ethyl-N-(2,6-difluorophenyl)pyrrolo[1,2a]benzimidazole-3-carboxamide, or 1,2-dihydro-2-oxo-N-(2,4-difluorophenyl)pyrrolo[1,2-a]benzimidazole- 3-carboxamide.

9. The compound of claim 8, selected from either of 1,2-dihydro- 2-oxo-N-(4-dimethylaminophenyl)pyrrolo[1,2-a]benzimidazole-3-carboxamide or 1,2-dihydro-2-oxo-N-(2,6-difluorophenyl)pyrrolo[1,2-a]benzimidazole-3-carboxamide.

10. A pharmaceutical composition comprising a compound of formula I:

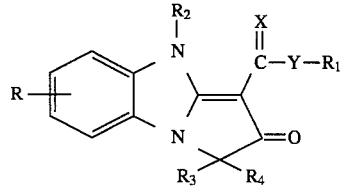

I wherein $R_1$ is selected from any of alkyl ($C_1$–$C_{12}$), cycloalkyl ($C_3$–$C_{10}$), phenyl, substituted phenyl, aralkyl, substituted aralkyl, a heterocycle wherein the heterocycle is selected from any of pyridine, thiazole, thiophene, furan, indole, benzothiophene, pyridazine, pyrimidine, indole, indoline, quinoline, indazole, imidazole, benzofuran, triazine, pyrazine, isoquinoline, isoxazole, thiadiazole, benzothiazole, triazole or benzotriazole, a substituted heterocycle, piperidin-3-yl, piperidin-2-yl, morpholin-4-yl, heterocyclic—$CH_2$, heterocyclic—$CH_2CH_2$—, or substituted heterocyclic—$CH_2$— and heterocyclic—$CH_2CH_2$—;

$R_2$ is selected from any of hydrogen, alkyl ($C_1$-$C_{12}$), cycloalkyl ($C_3$-$C_{10}$), aralkyl and substituted aralkyl;

R may be one or more substituents selected from the group consisting of any of hydrogen, alkyl ($C_1$-$C_8$), halogen, perfluorolower alkyl, lower alkoxy, di(lower alkyl)amino, lower alkoxycarbonyl or lower alkylthio;

X is selected from oxygen or sulfur;

Y is selected from NH, oxygen or sulfur;

Y and $R_1$ may also be taken together to form an $NH_2$ group;

in the case of substituted phenyl and substituted aralkyl, there are one or more substituents which are independently selected from any of halogen, alkyl ($C_1$-$C_5$), perfluoro(lower)alkyl, nitro, lower alkoxy, hydroxy, amino, lower alkylamino, di(lower alkyl)amino, carboxy, lower alkoxycarbonyl, carboxamido, lower alkylthio, cyano, or aminosulfonyl;

in the case of substituted heterocycle and substituted heterocyclic—$CH_2$— and heterocyclic—$CH_2CH_2$—, there are one or more substituents, which are independently selected from any of halogen, perfluoro (lower) alkyl, nitro, lower alkylthio, lower alkoxy, lower alkyl, di(lower alkyl) amino, carboxy, or lower alkoxycarbonyl, or a pharmaceutically acceptable salt, isomer or hydrate thereof.

in an amount effective for treating disorders of the central nervous system and a pharmaceutically acceptable carrier or diluent.

11. A method for treating disorders of the central nervous system comprising administering a compound of the formula I:

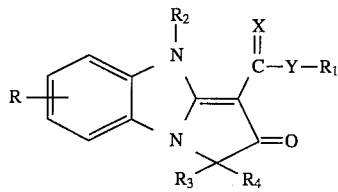

wherein $R_1$ is selected from any of alkyl ($C_1$-$C_{12}$), cycloalkyl ($C_3$-$C_{10}$), phenyl, substituted phenyl, aralkyl, substituted aralkyl, a heterocycle wherein the heterocycle is selected from any of pyridine, thiazole, thiophene, furan, indole, benzothiophene, pyridazine, pyrimidine, indole, indoline, quinoline, indazole, imidazole, benzofuran, triazine, pyrazine, isoquinoline, isoxazole, thiadiazole, benzothiazole, triazole or benzotriazole, a substituted heterocycle, piperidin-3-yl, piperidin-2-yl, morpholin-4-yl, heterocyclic—$CH_2$—, heterocyclic—$CH_2CH_2$—, or substituted heterocyclic—$CH_2$— and heterocyclic—$CH_2CH_2$—;

$R_2$ is selected from any of hydrogen, alkyl ($C_1$-$C_{12}$), cycloalkyl ($C_3$-$C_{10}$), aralkyl and substituted aralkyl;

R may be one or more substituents selected from the group consisting of any of hydrogen, alkyl ($C_1$-$C_8$), halogen, perfluorolower alkyl, lower alkoxy, di(lower alkyl)amino, lower alkoxycarbonyl or lower alkylthio;

$R_3$ and $R_4$ are selected from hydrogen, alkyl ($C_{1-3}$);

X is selected from oxygen or sulfur;

Y is selected from NH, oxygen or sulfur;

Y and $R_1$ may also be taken together to form an $NH_2$ group;

in the case of substituted phenyl and substituted aralkyl, there are one or more substituents which are independently selected from any of halogen, alkyl ($C_1$-$C_5$), perfluoro(lower)alkyl, nitro, lower alkoxy, hydroxy, amino, lower alkylamino, di(lower alkyl)amino, carboxy, lower alkoxycarbonyl, carboxamido, lower alkylthio, cyano, or aminosulfonyl;

in the case of substituted heterocycle and substituted heterocyclic—$CH_2$— and heterocyclic—$CH_2CH_2$—, there are one or more substituents, which are independently selected from any of halogen, perfluoro (lower) alkyl, nitro, lower alkylthio, lower alkoxy, lower alkyl, di(lower alkyl) amino, carboxy, or lower alkoxycarbonyl, or a pharmaceutically acceptable salt, isomer or hydrate thereof, to a mammal afflicted with a disorder of the central nervous system in an amount effective for treating such disorder.

12. The method of claim 11, wherein the effective amount is of from about 0.2 to 25 mg/kg per day.

13. The method of claim 11, wherein the disorder is anxiety.

14. The method of claim 11 wherein the disorder is convulsions.

15. The method of claim 11 wherein the disorder is sleeplessness.

16. The method of claim 11 wherein the disorder is muscle spasm.

17. The method of claim 11 wherein the disorder is benzodiazepine drug overdose.

* * * * *